United States Patent
Johal

(10) Patent No.: US 7,425,439 B2
(45) Date of Patent: Sep. 16, 2008

(54) METHOD FOR DISSOCIATION OF CELLS

(75) Inventor: Sarjit Johal, Iowa City, IA (US)

(73) Assignee: Grain Processing Corporation, Muscatine, IA (US)

( * ) Notice: Subject to any disclaimer, the term of this patent is extended or adjusted under 35 U.S.C. 154(b) by 328 days.

(21) Appl. No.: 10/919,191

(22) Filed: Aug. 16, 2004

(65) Prior Publication Data

US 2005/0100881 A1 May 12, 2005

Related U.S. Application Data

(60) Provisional application No. 60/495,750, filed on Aug. 15, 2003.

(51) Int. Cl.
*C12N 1/06* (2006.01)
(52) U.S. Cl. .................................................. 435/259
(58) Field of Classification Search ................. 435/259
See application file for complete search history.

(56) References Cited

U.S. PATENT DOCUMENTS

| 3,585,179 A | 6/1971 | Hiroshi et al. |
| 3,821,080 A | 6/1974 | Kalina et al. |
| 5,552,145 A * | 9/1996 | Toride et al. .............. 424/245.1 |
| 5,765,135 A | 6/1998 | Friedman et al. |
| 6,544,510 B2 * | 4/2003 | Olshenitsky et al. ....... 424/93.3 |

FOREIGN PATENT DOCUMENTS

| GB | 1432039 | 4/1976 |
| GB | 2006823 | 5/1979 |
| GB | 1582397 | 1/1981 |
| GB | 2221829 | 2/1990 |
| JP | 48032672 | 5/1973 |
| WO | WO 02/091850 | 11/2002 |

OTHER PUBLICATIONS

Nishikawa et al. Koshien Daigaku Kiyo, A: Eiyogakibi-hen (2003), vol. date 2002, 30, 9-14. (English abstract).*
Talaro et al. Foundations in Microbiology. 1993. pp. 272-275.*

* cited by examiner

*Primary Examiner*—Vera Afremova
(74) *Attorney, Agent, or Firm*—Banner & Witcoff Ltd.

(57) ABSTRACT

Disclosed is a method for the dissociation of cells. Cells are processed under conditions of pH, temperature, and shear to thereby yield a mixture of cell wall ghosts and cytoplasm. Preferably, the cells are jet cooked at an alkaline pH to form an intermediate mixture, and the intermediate mixture is subsequently jet cooked. Generally, the cells become dissociated, whereby at least one separate cell wall component is substantially separate from the dissociated cell walls.

16 Claims, 1 Drawing Sheet

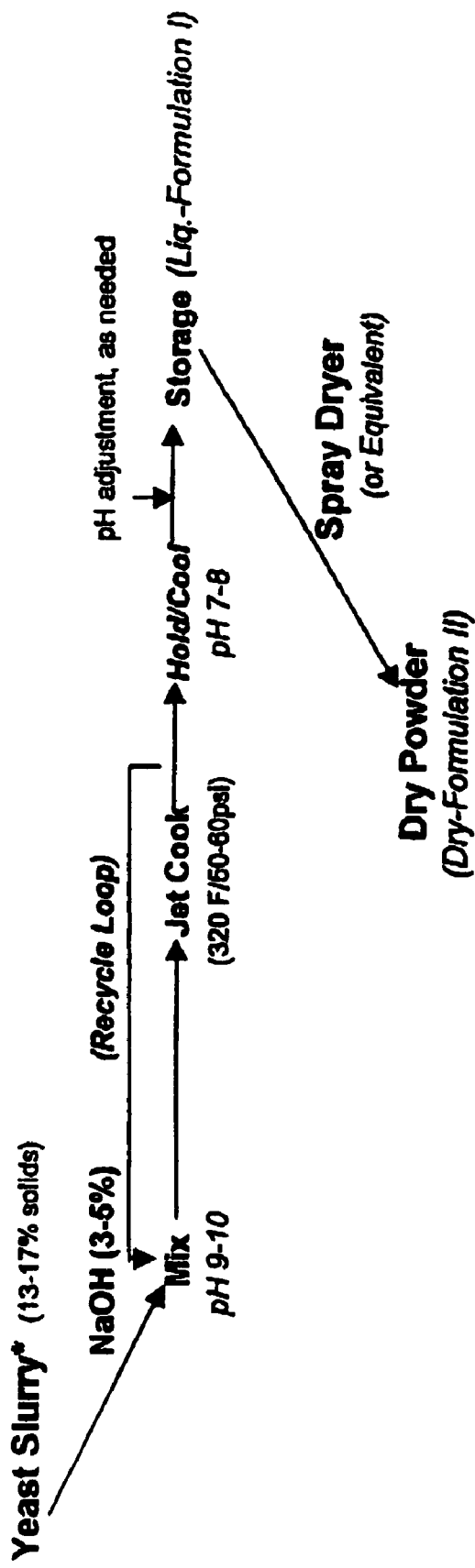

METHOD FOR DISSOCIATION OF CELLS

RELATED APPLICATION

This application claims the benefit of prior provisional application Ser. No. 60/495,750, filed Aug. 15, 2003, the teachings of which application are hereby incorporated by reference.

FIELD OF THE INVENTION

The invention pertains to the dissociation of cells to obtain nutrients and other commercially useful products therefrom.

BACKGROUND OF THE INVENTION

Yeast and yeast metabolites are widely used in an array of food and feed products. Baker's and brewer's yeast, for example, are excellent sources of nutrients and flavoring agents. Nutrients that are obtainable from cells include insoluble and soluble cell wall polysaccharides, oligosaccharides, glucans, proteins, peptides, nucleotides, and the like. Cells, in particular cell walls, are also thought to absorb pathogens and consequently to provide a measure of prophylaxis against infection.

Live cells, whole lysed cells, and cell fractions are of particular value in feed and pet food formulations. Lysed cells and cell fractions are thought to contain many nutritive components in a form that is bio-available to the consuming animal. Live yeast cells are thought to aid in digestion in ways not fully understood at present. Whole dead cells, on the other hand, are not thought to be of particular nutritive benefit, except possibly in ruminant animals. The digestive tract of monogastric animals is essentially unable to rupture the cell wall, and thus the majority of the dead cells pass through the digestive tract and are typically excreted whole, without releasing nutrients to the animal.

Consequently, if it is desired to obtain nutrients from dead yeast cells, generally it is necessary to rupture the walls of the cells to allow release of the nutrients. A number of methods are known for rupturing yeast cells, these including mechanical, hydrolytic and autolytic methods. Mechanical methods typically are employed in small-scale laboratory applications. Conventional mechanical disruption includes presses, such as the French press; homogenizers; sonic disruptors, and so forth. In a laboratory French press, for example, pressures as high 20,000 psi and high shear conditions are produced by passing the cells through a small orifice. Other devices subject the cell to different stresses but provide the same result, that is, rupture of the cell wall. For instance, another known apparatus, the bead beater, contains ceramic or glass pellets that are used to crush, shear and fracture cells. Hydrolytic procedures employ enzymes, acid, or alkali to rupture the cell walls. Cell autolysis is a well-known process wherein the yeast cell is subjected to digestion by its own enzymes.

Heretofore, it is believed that it has been difficult to extract nutrients from cells on a commercial scale, particularly from dead yeast cells, in light of certain drawbacks with the foregoing conventional methods. Mechanical rupture is attractive because the cell constituents are not contaminated with extraneous chemicals and additives. However, the costs associated with scaling-up and implementing such systems are considerable, as has been heretofore recognized. For instance, U.S. Pat. No. 5,756,135 issued to Seeley discusses some of the technological and economical challenges associated with commercial-scale production of a water insoluble yeast. Hydrolytic methods are more amenable to scale-up, but most such methods also have shortcomings such as high cost, long process time, or degradation/denaturation of specific nutrients.

Accordingly, most yeast cell hydrolyzates are produced commercially by autolysis. Yeast autolysis entails a slow reaction, however. An autolysis reaction requires an operating temperature that ranges from about 40° C. to 60° C., typically temperatures of 50° C.-55° C. At these or higher suitable temperatures, the reaction still requires a substantial period of time ranging from several hours to days to obtain a suitable degree of digestion. In an effort to accelerate the autolysis reaction, the prior art has taught to employ plasmolyzing agents, examples of which include organic solvents, salts and hydrolytic enzymes such as protease and lipases. Nonetheless, the autolysis reaction remains lengthy and commercially unwieldy.

A further drawback with autolysis is that the autolysis process is amenable only for use with living cells. Dead cells cannot be autolyzed. In recognition of this requirement, dedicated yeast manufacturers who desire to autolyze the yeast cells are required to take steps to preserve cell viability. In other industries where substantial quantities of live yeast are produced as a by-product, such as the brewing industry, live cells can be harvested economically and can be subjected to autolysis. However, certain industrial processes generate a substantial quantity of dead yeast by-product that cannot be subjected to autolysis. This is a particular problem in the production of distilled ethanol products, wherein the distillation process kills the yeast cells, thereby rendering the cells impossible to autolyze.

Accordingly, given the heretofore described drawbacks with mechanical and hydrolytic methods, it is very difficult to produce a cost-effective, high-volume yeast-derived feed or industrial product from such dead cells. In practice, the dead yeast cells themselves are sold as whole cells, typically into the ruminant animal feed markets.

It would be desirable to provide a method for disassociating yeast and other cells in a manner that allows for rupture of the walls of the cells to release the cell cytoplasm therefrom. It would be of particular benefit for such method to be applicable to dead cells in addition to live cells. Such method would find a particular applicability in the distilled ethanol industry, but would also be useful in connection with numerous other industries.

THE INVENTION

It has now been found that yeasts, fungi, bacteria, and other cells (including eukaryotic cells) may be processed to recover soluble or insoluble cell components such as proteins, saccharides, peptides, lipids, glucans, and the like. Generally, the cells are processed by a shearing force in the presence of an alkaline pH and heat (i.e. temperatures above 25° C.).

In accordance with the invention, a method for dissociating cells is provided. In one embodiment of the invention, conditions of pH, shear, and temperature suitable for dissociation of the cell are selected, the conditions being suitable for dissociation whereby at least one soluble dissociated molecular cell wall component is substantially separable from the dissociated cells. The method is intended to at least substantially completely dissociate the cell walls, but the cells are not dissociated to such an extent that the molecular constituents of the cell walls are reduced to simple molecules. The soluble dissociated cell wall component may be separated from the dissociated cells.

In accordance with preferred embodiments of the invention, a method for providing a mixture of cell wall ghosts and cytoplasm is provided. The method includes subjecting the cells to heat, shear, and pH under conditions sufficient to rupture the cell walls and to allow the release of cytoplasm therefrom while leaving a substantially intact cell wall ghost. The method most preferably comprises jet cooking the cells. In the most highly preferred embodiments of the invention, the cells are jet cooked to form an intermediate product, and the intermediate product is subsequently jet cooked to form the mixture of cytoplasm and cells. The mixture thus formed may be spray dried or otherwise treated, such as by substantially separating the cell walls from the cytoplasm. An animal feed may be prepared from the mixture or spray dried mixture thus formed.

BRIEF DESCRIPTION OF THE FIGURE

The FIGURE is a schematic illustration of a yeast cell wall dissociation method.

DETAILED DESCRIPTION OF THE PREFERRED EMBODIMENTS

The following paragraphs will focus primarily on the dissociation of yeast cells, but it should be understood that the invention is not limited thereto. Indeed, the invention is deemed to be applicable to any prokaryotic or eukaryotic cells, in particular microbial cells, and especially to yeasts. Other cells suitable for dissociation in connection with the present inventive method include fungi, plant cells, spores, and like microorganisms. More generally, any cell that can be "harvested" to provide nutrients or other chemically useful materials can be used in conjunction with the invention. If yeast is used, the yeast is preferably a strain of *Saccharomyces cereviasiae*, including those strains commercially sold as brewer's yeasts and baker's yeasts. The cells may be alive or dead, or mixtures of live and dead cells may be employed. The yeast cells may be used as supplied from a commercial distilling operation, or may be washed prior to use in conjunction with the invention to remove bittering agents, fermentation insolubles, and the like. It is contemplated that the yeast may include fiber carbohydrate, or other material from a commercial ethanol distilling operation, and in some embodiments of the invention the yeast source may comprise stillage. A preferred yeast source is spray dried yeast.

In accordance with the invention, the walls of cells are dissociated to yield cell wall components. The dissociation contemplates a wide range of dissociation of the cell walls, and the extent of dissociation may be selected by one of skill in the art. For instance, the cells as received may contain impurities or non-native components that are bound via electrostatic forces (or even covalent bonds) to the cell walls. The dissociation in some embodiments of the invention contemplates removal of these impurities or non-native components. In preferred embodiments of the invention, the cell walls are partially disintegrated, such that some native cell wall components have been liberated from the molecular structure of the cell walls, but that the cell wall ghosts are still discernable as discrete entities under microscopic examination. It is thus contemplated that the ghosts may not be complete cell walls, inasmuch as some of the original components of the cell wall may have become dissociated from the remaining components of the cell wall. Any portion of native cell wall components may be so liberated, such as 10%, 20%, 30%, 40%, 50%, 60%, 70%, 80%, or 90%, whereby in such embodiments, the cell wall ghosts are still discernable. In less preferred embodiments of the invention, the dissociation is completed to an extent such that the cell walls are substantially completely or fully disintegrated, such that the cell walls are not visible as discrete entities under microscopic examination.

Generally, in accordance with the preferred embodiments of the invention, the method for rupturing cells comprises subjecting the cells to heat, pH, and shear under conditions sufficient to rupture the walls of at least some of the plurality of the cells to allow cytoplasm to be released therefrom, thereby forming a mixture of ghosts and cytoplasm. The mechanism of action of the present invention is believed to be non-specific degradation or of the cells, whereby oligosaccharides (such as mannanoligosaccharides) and glucans are released. Upon such degradation, the walls of the cells weaken eventually to the point of cell wall rupture to thereby release the cytoplasm contained therein. It is contemplated that conditions of temperature, pH, shear, and residence time in a suitable apparatus will vary widely from species to species of the cell and will further vary depending upon the apparatus chosen. Generally, it is contemplated that the temperature employed will be in a range of from 140° to 160° C.

To hydrolyze the cell walls, a slurry of the yeast may be prepared by known techniques, such as evaporation or known liquid-solid separation techniques, or alternatively the yeast may be dried and subsequently mixed with water to form a slurry. The solids content of the starting yeast slurry is preferably about 5 to 25% (w/v), preferably 10 to 20%, and more preferably 12 to 18%. It is desired to employ the solids content as high as is practicable, and an upper limit of 18 to 20% is deemed most commercially practicable.

In carrying out the inventive method, the pH of the slurry of yeast is adjusted to any suitable pH, preferably a pH between 8.0 and 12.0, more preferably 9.0 to 11.0, and most preferably 9.5 to 10.0, using an alkali agent, most preferably a food-grade alkali such as sodium hydroxide, calcium hydroxide, or potassium hydroxide. The invention is not limited to processing under alkaline conditions. In some embodiments, strongly acidic conditions, preferably pH 0.5 to 3, and more preferably pH 1 to 2, may be employed. The preferred acidifying agent is a food-grade acid, such as hydrochloric, phosphoric, sulfuric, or mixtures thereof. Because it is believed in most instances that an acid pH is far more aggressive than the relatively mild alkaline conditions that may be employed for alkali hydrolysis of the yeast, alkaline conditions are preferred in connection with the present invention.

The alkaline slurry of yeast is then subjected to shearing under conditions sufficient to rupture the walls of at least some of the plurality of the yeast cells to thereby release the cytoplasm. Generally, the cells may be subjected to a pressure of between 35 to 105 psig at the conditions of temperature, pH, and shear heretofore discussed. The cells are preferably subjected to such pressure for a time ranging from 10 to 150 seconds. Once again, this parameter will be expected to vary with the other operating parameters.

Any suitable apparatus may be employed in connection with the invention. In accordance with highly preferred embodiments of the invention, a jet cooking apparatus is employed. A jet cooking apparatus resembles a jet pump that is employed to move liquids and slurries. In the jet cooking process, high pressure saturated steam, at a pressure that ranges from about 60 to 200 psig, is injected through a nozzle into the center of a venturi mix combining tube. The slurry is then pulled into the annular gap formed by the steam nozzle and the venturi opening. The slurry is heated as it accelerates to sonic velocity within the mixing tube. While passing through the mixing tube, the cells are subjected to extremely turbulent conditions which cause partial hydrolysis of the cell walls.

It is contemplated in preferred embodiments of the invention that multiple passes through a jet cooking apparatus, preferably between 2 to 5 passes, and more preferably 2 to 3 passes, will be employed. If it is desired to completely liquefy the cells, i.e., to disassociate the cells to an extent such that the cell walls are substantially completely dissociated with no intact ghosts remaining, a higher number of passes, such as 3 to 7, may be employed. The precise number of passes required to achieve complete dissociation and the number of passes required to achieve a mixture of cytoplasm and ghosts will depend upon the specific apparatus employed and on the other operating conditions.

Generally, it is believed that the more aggressive conditions that are employed, such as higher alkalinity and temperature, the fewer the number of passes will be needed to liquefy greater than 90% of the cells. The pH of the slurry will decline after each pass through the jet cooking apparatus, at least because of the introduction of additional water via the steam injector, and possibly because of hydroxyl uptake. It is contemplated that additional alkaline agents may be added after each pass, but preferably no such agents are added.

The jet cooking may be practiced as a batch process or as a continuous process. In either event, the intermediate product formed upon the first jet cooking pass is preferably held for a retention time ranging from 30 seconds to 1 hour. Most preferably, the intermediate product is held at a temperature of 140° to 160° C. and a pressure of 50 to 80 psig, then flashed to atmospheric pressure before the second or subsequent jet cooking pass. After the final jet cooking step, preferably there is no retention period, although such may optionally be employed. If the product is jet cooked over more than two passes, the intermediate products prepared after the first pass but before the final pass may be held for a retention period, or the retention period may be omitted.

In accordance with some embodiments of the invention, a mild, one- or two-pass slightly alkaline pretreatment can be employed to slightly dissociate the cells. After such pretreatment, the alkaline liquid can then be removed, and a slurry of cells formed by adding water. The cell slurry then may be adjusted to the acidic or alkaline conditions heretofore discussed, and the slurry then may be jet cooked. It is contemplated that the mild alkaline pretreatment will remove contaminating biomolecules, small metabolites, and related fermentation broth products that may contribute off-flavors or colors or may otherwise negatively affect the hydrolyzed cells.

The mixture of cytoplasm and ghosts thus formed is itself deemed to be a commercially valuable product. It is believed that this mixture typically will have a solids content that ranges from about 17 to 20%, with about 35% of the solids content comprising insoluble materials and the rest comprising soluble materials. The product mixture thus formed may be treated in any manner desired. For instance, the soluble portion of the material may be at least substantially separated from the insoluble portion, such as by centrifugation. The solids material will comprise largely cell wall ghosts, and the cell wall ghosts may be sold commercially. The liquid fraction may be further treated, for instance, by spray drying the liquid fraction with a suitable carrier. In some embodiments of the invention, the mixture exiting the jet cooker may itself be spray dried, with or without a carrier. Any suitable spray drying carrier may be employed in connection with the invention, such as maltodextrins, reduced maltodextrins, starches, starch hydrolyzates, and so forth.

The invention contemplates a method for feeding an animal, the method comprising feeding the animal a product mixture prepared in accordance with the foregoing teachings. The animal also may be fed a fraction of the mixture heretofore described, for instance, the solids fraction or the liquid fraction that remains after centrifuging the product mixture. Generally, the animal will be fed an animal feed, which includes the mixture heretofore described (or a suitable fraction thereof) in combination with one or more animal nutritive sources. The mixture or fraction prepared in accordance with the present invention may be added in any amount relative to the other components of the animal feed. Preferably, the mixture or fraction is added in an amount that ranges from 0.01 to 25% by weight, although a greater or lesser range is also contemplated. The invention is deemed to find particular applicability in feeds for swine, ruminants, poultry, and household pets such as cats and dogs, although it is contemplated that the invention may find utility in connection with feeds for other animals. In some embodiments of the invention, the mixture prepared in accordance with the foregoing teachings, or a fraction of such mixture, may be used in connection with human food products. It is believed that the cytoplasm will provide nutritive benefit to swine and ruminants, and, surprisingly, it was found in one experiment that swine prefer food products prepared in accordance with the foregoing teachings to similar food products prepared with a commercially available yeast derivative.

The present invention is deemed to allow the hydrolysis of cell walls without the need for mechanical, autolytic, or hydrolytic procedures. Nonetheless, in some embodiments of the invention, autolysis or hydrolysis procedures may be employed in conjunction with the procedures heretofore described. In such cases, it is contemplated that the dissociation afforded by the invention may decrease incubation time, and/or may improve enzymatic hydrolysis. Although it is not intended to limit the invention to a particular theory of operation, it is believed that such other procedures may so operate by exposing additional proteins, lipids, or carbohydrates on the cell surface. For similar reasons, the dissociation afforded by the invention may be used in conjunction with acid or alkaline hydrolysis procedures by weakening the cell wall prior to such processing.

The invention contemplates the selection of conditions of temperature, pH, and shear to achieve the results desired. By selection of appropriate conditions, the manner of cell dissolution may be controlled with precision. For instance, if desired, dissociation of the cell wall and release of cytoplasmic components without extensive denaturation of the constituent biomolecules may be achieved. Alternatively, if more rigorous conditions are employed, the cell walls may be dissociated to an extent whereby only the robust soluble or insoluble molecules, such as alkali-insoluble betaglucans, chitin and the like, remain after processing. In some embodiments, the invention may be employed to dissociate cell walls and to harvest oligosaccharides that are obtained therefrom, with or without rupture of the cell walls.

The following Examples are provided to illustrate the invention but should not be construed as limiting the scope of the invention.

EXAMPLE 1

This Example illustrates the jet cooking of dried yeast cells in a skid-mounted jet cooking pilot scale apparatus.

About 1.8 kg of commercial spray-dried dead Brewer's yeast was added to about 10 L of cold water with agitation in a mixing tank. After about 5 minutes an additional quantity of water was added to bring the final volume to about 12 L. The slurry was allowed to mix for another 3 to 5 minutes at which time about 500 ml of about 20% concentrated sodium hydroxide was slowly added to the yeast slurry. The agitation was adjusted to high speed mixing during and immediately following the alkaline addition. The moisture was allowed to mix at the high speed for another 5 to 10 minutes whereupon the pH was checked. The measurement showed that the pH had increased to about 9.2. Another small addition of 20% sodium hydroxide was used to increase the pH to about 9.7. The slurry was allowed to mix for another 3 minutes or so at a high rate of speed at which time the agitation was reduced.

The mixing tank, which was an integral component of the skid mounted jet cooker assembly, was connected to a jet cooker by a valve and piping. At the appropriate time the valve was opened and the slurry pumped to the cooker. The cooker was calibrated at 320° F. After a residence time in the jet cooker of about 3 minutes, the slurry exited the cooker and was collected (Pass 1). After most of the final material had entered the cooker piping, and the mixing tank emptied, the intermediate product thus formed was transferred to the mixing tank and pumped through the cooker again (Pass 2). The sample was then collected as it exited the assembly and set aside to cool.

The mixture thus formed demonstrated clear microscopic confirmation of cell dissociation as evidenced by the presence of cells wall ghosts. After the first pass through the jet cooker, about 10 to 20% of such cell wall ghosts were observed. After the second pass, approximately 60 to 70% of the cells typically appeared as ghosts.

Some attributes of the processed material are shown in the following table. In this table, reported viscosity was measured using a Brookfield viscometer at room temperature (spindle nos. 1, 2, 3, and 5 were used for the respective samples).

| Sample | PH | Viscosity |
|---|---|---|
| Yeast Slurry | 4.3 | 38 cP |
| Adjusted Slurry | 10.0 | 177 cP |
| Jet Cooked Intermediate Product | 9.1 | 633 cP |
| Final Jet Cooked Mixture | 8.0 | 2230 cP |

This data suggests that the rupture of the dead yeast cells is accompanied by a concomitant change in viscosity (increase) and pH (decrease). These changes are interpreted as signaling the pasting and deterioration of the cell wall, and associated release of wall components such as glucans and oligosaccharides. The release of glucans and oligosaccharides was believed to be responsible for the increase in viscosity.

EXAMPLE 2

A post-distillation fermentation broth from an ethanol production plant was centrifuged and the solids recovered as a slurry. This slurry was composed of about 20% solids which included primarily (80 to 90%) dead Brewer's yeast cells. The slurry was spray-dried in a pilot plant dryer and stored at room temperature. This material was later retrieved from storage and processed employing the general parameters and multiple pass jet cook procedures outlined in Example 1 and illustrated in FIG. 1 using the skid mounted laboratory/pilot plant jet cooking apparatus.

The observations and results of this experiment were consistent with other experiments performed in this manner. Specifically, some (10-20%) dead yeast cell wall dissociation, an increase in viscosity, and a decrease in pH were observed in the first jet cooker pass. Immediately following the first pass of the entire sample volume, this material was transferred back to the jet cooker feed tank and cycled through again. After the second pass, the viscosity increased dramatically, the pH declined further and a significant number of the yeast cells appeared as distended or swollen cell walls. Cell debris which were not particularly evident in the unprocessed sample or the first pass material were also clearly evident.

EXAMPLE 3

This example illustrates the purification of fungal chitin using the method of the invention and a substantially uniform microbial fungal source.

A fungal biomass such as *Aspergillus niger* or *Aspergillus oryzae* is concentrated (or dewatered) using a known procedure such as evaporation, centrifugation and the like to about 12 to 17% solids. The pH of the slurry is adjusted to about pH 11 to 12 with about 5 to 10% sodium hydroxide. The slurry is then jet cooked at 320° F., 50 to 60 psi. The first pass is collected and the pH readjusted to 11 to 12, as needed. This material is then subjected to as many jet cook cycles at the strongly alkaline pH as required to effect hydrolysis of as much of the protein, lipids, glucan and other biomolecules as possible. The treated material is next filtered using vacuum filtration or a related procedure to remove denatured biomolecules and undesirable materials. The filtered (or alkali insoluble) material is washed with water, the pH is adjusted and available for use as a substrate for the production of glucosamine and the like.

EXAMPLE 4

Several thousand pounds of dead brewer's dried yeast obtained from a commercial ethanol distilling operation were treated in accordance with the present invention to prepare mixtures of cell wall ghosts and cytoplasm. To prepare the mixtures, the following procedures were employed.

A 17% yeast slurry was prepared by adding dried dead yeast to water with agitation. After about 10 to 20 minutes of aggressive agitation, the pH of the mixture was adjusted to a pH in the range of 9.5 to 10.0 with 50% NaOH. Two jet cookers were allowed to attain temperatures of about 300° F. The jet cookers were arranged in an in-line configuration.

The yeast slurry was fed into the primary jet cooker at a rate of about 1.5 gal/min. The output for this cooker was held for 12 to 15 min. at a temperature of about 150° C. and a pressure of 50 to 80 psig, flashed to ambient pressure, then fed directly into the second jet cooker. The jet cooking operations were conducted to maintain a constant flow from the primary to the secondary jet cooker. The output from the second jet cooker was then collected in a holding vessel. After cooling to a temperature of about 60° to 70° C, the pH of the collected material was lowered from about pH 7 to about pH 4.0 with hydrochloric acid.

A preservative (sodium benzoate) was then added in an amount of 0.8% by weight to minimize microbial growth during transport and storage to a spray drying facility. Approximately 40 to 50 hours after jet cooking was completed, the product mixture of cell wall ghosts and cytoplasm was viscous but still fluid product. This product was spray dried in a box dryer. No additional carrier was employed. The spray dried material was evaluated and found to have a moisture content of about 5%.

The spray dried mixture was collected and packaged in 50 lb. paper bags. Several hundred such bags were prepared and were stored at room temperature.

Samples of the jet cooked material (before spray drying) were collected throughout the duration of the run and viewed microscopically. Both these cooked and those prepared in accordance with the laboratory procedure of Example 1 exhibited substantially identical morphology. It was found that 80 to 90% of the cells had been ruptured to yield cell wall ghosts. These ghosts were observed to exhibit evidence of cell wall disruption, including distension, loss of rigidity, non uniformity of size and shape, and so forth.

EXAMPLE 5

The spray dried mixture prepared in accordance with Example 4 was analyzed to yield the following approximate composition. Whole uncooked yeast was also analyzed. It is seen that a portion of the nutritive material in the yeast remained substantially unaffected by the jet cooking process, and that the jet-cooked mixture could provide nutritive benefit.

|  | Dried Yeast (Whole) | Jet cooked mixture |
|---|---|---|
| Protein | 45.8 | 44.57 |
| Fiber, Crude | 3.6 | 2.9 |
| Ash | 4.5 | 9.22 |
| Fiber, Dietary, Total | 20.4 | 19.7 |
| Try | 0.48 | 0.48 |
| Cys | 0.46 | 0.33 |
| Met | 0.69 | 0.48 |
| Asp | 4.56 | 5.97 |
| Thr | 2.11 | 2.2 |
| Ser | 2.25 | 2.25 |
| Glu | 6.83 | 5.77 |
| Pro | 2.32 | 2.48 |
| Gly | 1.95 | 1.87 |
| Ala | 3.45 | 2.98 |
| Val | 2.45 | 2.48 |
| Iso | 2.09 | 1.99 |
| Leu | 4.03 | 3.84 |
| Tyr | 1.54 | 1.58 |
| Phe | 2.15 | 2.02 |
| Lys | 2.61 | 2.13 |
| His | 0.96 | 0.96 |
| Arg | 1.97 | 1.44 |
| Vit. A | 9,350 | 5,800 |
| Vit B1 | 7.62 | 2.78 |
| Vit. B2 | 11.8 | 6.8 |
| Vit. B6 | 1.56 | 1.15 |
| Vit. B12 | <.002 | 0.0039 |
| Vit. E | <3.0 | <3.0 |
| Ca | 0.027 | 0.08 |
| Mg | 0.16 | 0.21 |
| P | 0.84 | 1.06 |
| K | 0.68 | 0.83 |
| Na | 0.12 | 2.35 |
| Cu | <.0002 | 0.00051 |
| Fe | 0.0034 | 0.006 |
| Mn | 10 | 9.6 |
| Zn | 56 | 46 |

EXAMPLE 6

Two commercial swine feed formulations, designated herein as formulations A and B, were obtained. The spray dried yeast mixture prepared in accordance with Example 4 was added to each of the commercial animal feed formulations to form modified formulations A1 and B1. For comparison, a commercial yeast derivative was also added to each of the two commercial swine feeds to form modified formulations A2 and B2. The commercial yeast derivative product was composed of cell wall ghosts believed to have been prepared by autolysis, in combination with fermentation solubles. The commercial yeast derivative was added to the two commercial animal feeds in an amount of 4 lbs. per ton, whereas the spray dried product prepared in accordance with Example 4 was added in an amount of 6 lbs. per ton to achieve a comparable loading of cell wall ghosts.

The modified feed formulations A1 and B1 (representing feeds prepared in accordance with the invention) and A2, and B2 (representing the comparative product) were fed to 100 pigs. The pigs were housed in ten separate pens, with ten pigs per pen. Each pen was provided with two feeders. The modified feed formulations A1 and A2 each were added to one of the feeders, and the amount of feed consumed by the pigs was measured after three days and after six days. The feeders were switched one time per day in an effort to eliminate any bias that may have been associated with the position of the feeder in the pen. In a separate experiment, the modified feed formulations B1 and B2 were added to the feeders, and the amount of feed consumed by the pigs was measured. The following results were observed.

|  | B1 | | A1 | | |
|---|---|---|---|---|---|
| Days | Lb/Pig | % | Lb/Pig | % | P-Value |
| 0-3 | .23 | 33 | .46 | 67 | <.01 |
| 0-6 | .35 | 18 | 1.60 | 82 | <.01 |

|  | B2 | | A2 | | |
|---|---|---|---|---|---|
| Days | Lb/Pig | % | Lb/Pig | % | P-Value |
| 0-3 | .12 | 26 | .34 | 74 | <.01 |
| 0-6 | .23 | 16 | 1.22 | 84 | <.01 |

Surprisingly, for both commercial swine feeds, the pigs exhibited a strong preference for the modified feed formulated with the product of Example 4 relative to the commercial cell wall product. This preference was manifest after three days and became more pronounced after six days. These results demonstrate that the pigs exhibited a strong preference for the feed that contained the material of Example 4. The improved palatability of this feed was seen to enhance feed uptake.

It is thus seen that the invention provides a method for dissociation of cells.

All references cited herein are hereby incorporated by reference. All methods described herein can be performed in any suitable order unless otherwise indicated herein or otherwise clearly contradicted by context. The use of any and all examples, or exemplary language provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-descried elements in all possible varia-

What is claimed is:

1. A method comprising:
   providing a plurality of microbial cells; and
   subjecting said cells to heat, pH, and shear under conditions sufficient to rupture the walls of at least some of said plurality of cells to allow cytoplasm to be released therefrom thereby forming a mixture of cell wall ghosts and cytoplasm, said cells being cooked in a jet cooking apparatus.

2. A method according to claim 1, said pH being an alkaline pH.

3. A method according to claim 2, said pH ranging from 8.5 to 10.5.

4. A method according to claim 3, said pH ranging from 9 to 10.

5. A method according to claim 1, said cells being subjected to a temperature ranging from 140 to 160° C.

6. A method according to claim 1, the method comprising;
   jet-cooking said mixture of cells in a jet-cooking apparatus to form an intermediate mixture; and
   jet-cooking said intermediate mixture to form said mixture of cell wall ghosts and cytoplasm.

7. A method according to claim 1, said cells comprising yeast cells.

8. A method according to claim 7, said cells comprising *S. cereviasiae* cells.

9. A method according to claim 1, further comprising at least substantially separating said cytoplasm from said cell wall ghosts.

10. A method according to claim 9, said separation being performed by centrifuging said mixture of cell wall ghosts and cytoplasm.

11. A method according to claim 1, further comprising spray drying said mixture of cytoplasm and cell wall ghosts.

12. A method comprising:
   providing a plurality of microbial cells;
   empirically determining, for said plurality of cells, conditions of heat, shear, and pH sufficient to rupture the walls of at least some of the plurality of cells to allow cytoplasm to be released therefrom to thereby yield a mixture of cell wall ghosts and cytoplasm; subjecting said cells to said heat and said shear and said pH under conditions sufficient to rupture the walls of at least some of said plurality of cells to allow cytoplasm to be released therefrom and to form a mixture of cell wall ghosts and cytoplasm;
   said cells being cooked in a jet cooking apparatus.

13. A method for the dissociation of microbial cells, comprising:
   providing microbial cells;
   dissociating said cells under conditions of pH, temperature, and shear to thereby yield a mixture of dissociated cell wall components, said conditions having been selected to be suitable for the at least partial dissociation of the walls of said cells, whereby at least one soluble dissociated molecular cell wall component is substantially separable from the dissociated cell walls, said cells being cooked in a jet cooking apparatus.

14. A method according to claim 1, said cells being subjected to steam.

15. A method for rupturing microbial cells to yield a mixture comprising cell wall ghosts and cytoplasm, comprising:
   providing a plurality of microbial cells; and
   subjecting said cells to heat, pH, and shear under conditions sufficient to rupture the walls of at least some of said plurality of cells to allow cytoplasm to be released therefrom thereby forming said mixture of ghosts and cytoplasm, said cells being subjected to a temperature ranging from 140° to 160° C., the method comprising:
   jet-cooking and mixture of cells in a jet-cooking apparatus to form an intermediate mixture; and
   jet-cooking said intermediate mixture to form said mixture of cell wall ghosts and cytoplasm.

16. A method according to claim 15, said cells being subjected to steam.

* * * * *